（12） United States Patent
Alarcon et al.

(10) Patent No.: US 12,337,104 B2
(45) Date of Patent: Jun. 24, 2025

(54) ELECTRONIC CIGARETTE

(71) Applicant: FONTEM VENTURES B.V., Amsterdam (NL)

(72) Inventors: Ramon Alarcon, Los Gatos, CA (US); Adam Hoffman, Campbell, CA (US); Michael Starman, Los Gatos, CA (US); Christopher Myles, San Jose, CA (US)

(73) Assignee: FONTEM VENTURES B.V., Amsterdam (NL)

( * ) Notice: Subject to any disclaimer, the term of this patent is extended or adjusted under 35 U.S.C. 154(b) by 0 days.

(21) Appl. No.: 18/455,381

(22) Filed: Aug. 24, 2023

(65) Prior Publication Data

US 2024/0058557 A1  Feb. 22, 2024

Related U.S. Application Data

(63) Continuation of application No. 15/930,061, filed on May 12, 2020, now abandoned, which is a (Continued)

(51) Int. Cl.
| | |
|---|---|
| *A61M 15/06* | (2006.01) |
| *A24F 40/10* | (2020.01) |
| *A24F 40/50* | (2020.01) |
| *A24F 40/51* | (2020.01) |
| *A61M 11/00* | (2006.01) |
| *A61M 11/04* | (2006.01) |

(Continued)

(52) U.S. Cl.
CPC .............. *A61M 15/06* (2013.01); *A24F 40/50* (2020.01); *A24F 40/51* (2020.01); *G01F 1/6888* (2013.01); *G01F 1/696* (2013.01); *H05B 1/0244* (2013.01); *A24F 40/10* (2020.01); *A61M 11/005* (2013.01); *A61M 11/042* (2014.02); *A61M 15/0025* (2014.02); *A61M 2016/0024* (2013.01); *A61M 2016/0039* (2013.01); *A61M 2205/587* (2013.01); *A61M 2206/11* (2013.01)

(58) Field of Classification Search
CPC .......... A24F 40/10; A24F 40/50; A24F 40/51; A61M 11/005; A61M 11/042; A61M 15/0025; A61M 15/06; A61M 2016/0024; A61M 2016/0039; A61M 2205/587; A61M 2206/11; G01F 1/6888; G01F 1/696; H05B 1/0244
USPC ........................................................ 392/404
See application file for complete search history.

(56) References Cited

U.S. PATENT DOCUMENTS

| | | | | |
|---|---|---|---|---|
| 3,931,736 | A | * | 1/1976 | Olmstead .............. G01F 1/6842 73/204.19 |
| 2015/0077981 | A1 | * | 3/2015 | Cormack ................ A24F 40/70 29/874 |
| 2016/0219938 | A1 | * | 8/2016 | Mamoun ................ G05B 15/02 |

* cited by examiner

*Primary Examiner* — Dana Ross
*Assistant Examiner* — Joseph W Iskra
(74) *Attorney, Agent, or Firm* — Perkins Coie LLP; Kenneth H. Ohriner

(57) ABSTRACT

In accordance with one aspect of the present invention there is provided an electronic smoking device comprising a flow channel and an atomizer. The flow channel can comprise an incoming airflow opening, an incoming airflow pathway, a sensor assembly, and an outgoing airflow opening. The atomizer can be fluidly coupled to the flow channel. The flow channel can be configured to direct an airflow from the incoming airflow opening, through the incoming airflow pathway, over the sensor assembly, and through the outgoing airflow opening. The electronic smoking device can further be configured to pass the airflow over the atomizer.

8 Claims, 13 Drawing Sheets

Related U.S. Application Data continuation of application No. 15/219,214, filed on Jul. 25, 2016, now Pat. No. 10,757,973.

(51) Int. Cl.
*A61M 15/00* (2006.01)
*A61M 16/00* (2006.01)
*G01F 1/688* (2006.01)
*G01F 1/696* (2006.01)
*H05B 1/02* (2006.01)

ELECTRONIC CIGARETTE

This application is a continuation of U.S. patent application Ser. No. 15/930,061, filed May 12, 2020, which is a continuation of U.S. patent application Ser. No. 15/219,214, filed Jul. 25, 2016, now U.S. Pat. No. 10,757,973, both of which are incorporated herein by reference.

FIELD OF INVENTION

The present invention relates generally to electronic smoking devices and in particular electronic cigarettes.

BACKGROUND OF THE INVENTION

An electronic smoking device, such as an electronic cigarette (e-cigarette), typically has a housing accommodating an electric power source (e.g., a single use or rechargeable battery, electrical plug, or other power source), and an electrically operable atomizer. The atomizer vaporizes or atomizes liquid supplied from a reservoir and provides vaporized or atomized liquid as an aerosol. Control electronics control the activation of the atomizer. In some electronic cigarettes, an airflow sensor is provided within the electronic smoking device, which detects a user puffing on the device (e.g., by sensing an under-pressure or an airflow pattern through the device). The airflow sensor indicates or signals the puff to the control electronics to power up the device and generate vapor. In other e-cigarettes, a switch is used to power up the e-cigarette to generate a puff of vapor.

In prior art eCigs, the pressure sensor is configured to sense a user's draw on the eCig and transmit an activation signal to the heating coil to vaporize the liquid solution. However, these pressure sensors can be large and costly.

SUMMARY OF THE INVENTION

In accordance with one aspect of the present invention there is provided an electronic smoking device comprising a flow channel and an atomizer. The flow channel can comprise an incoming airflow opening, an incoming airflow pathway, a sensor assembly, and an outgoing airflow opening. The atomizer can be fluidly coupled to the flow channel. The flow channel can be configured to direct an airflow from the incoming airflow opening, through the incoming airflow pathway, over the sensor assembly, and through the outgoing airflow opening. The electronic smoking device can further be configured to pass the airflow, at least in part, over the atomizer.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, the same element numbers indicate the same elements in each of the views.

DESCRIPTION OF THE PREFERRED EMBODIMENTS

Figure 1:
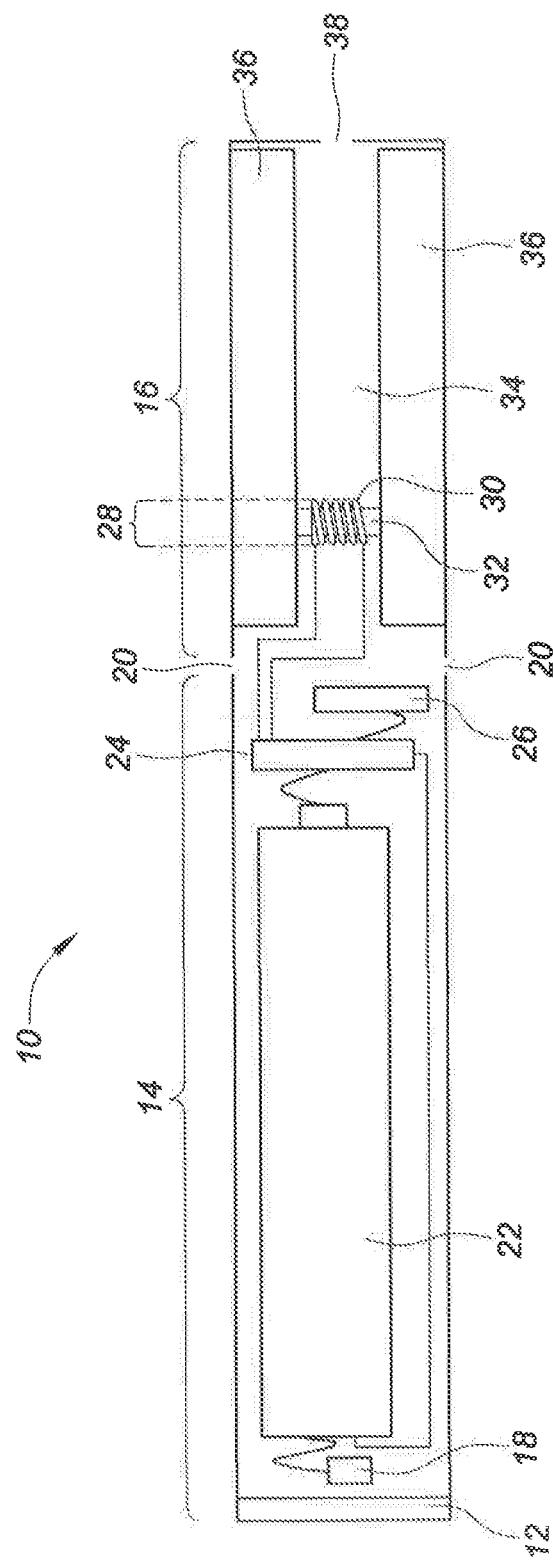
FIG. 1 is a schematic cross-sectional illustration of an exemplary e-cigarette.

Throughout the following, an electronic smoking device will be exemplarily described with reference to an e-cigarette. As is shown in FIG. 1, an e-cigarette 10 typically has a housing comprising a cylindrical hollow tube having an end cap 12. The cylindrical hollow tube may be a single-piece or a multiple-piece tube. In FIG. 1, the cylindrical hollow tube is shown as a two-piece structure having a power supply portion 14 and an atomizer/liquid reservoir portion 16. Together the power supply portion 14 and the atomizer/liquid reservoir portion 16 form a cylindrical tube which can be approximately the same size and shape as a conventional cigarette, typically about 100 mm with a 7.5 mm diameter, although lengths may range from 70 to 150 or 180 mm, and diameters from 5 to 28 mm.

The power supply portion 14 and atomizer/liquid reservoir portion 16 are typically made of metal (e.g., steel or aluminum, or of hardwearing plastic) and act together with the end cap 12 to provide a housing to contain the components of the e-cigarette 10. The power supply portion 14 and the atomizer/liquid reservoir portion 16 may be configured to fit together by, for example, a friction push fit, a snap fit, a bayonet attachment, a magnetic fit, or screw threads. The end cap 12 is provided at the front end of the power supply portion 14. The end cap 12 may be made from translucent plastic or other translucent material to allow a light-emitting diode (LED) 18 positioned near the end cap to emit light through the end cap. Alternatively, the end cap may be made of metal or other materials that do not allow light to pass.

An air inlet may be provided in the end cap, at the edge of the inlet next to the cylindrical hollow tube, anywhere along the length of the cylindrical hollow tube, or at the connection of the power supply portion 14 and the atomizer/liquid reservoir portion 16. FIG. 1 shows a pair of air inlets 20 provided at the intersection between the power supply portion 14 and the atomizer/liquid reservoir portion 16.

A power supply, preferably a battery 22, the LED 18, control electronics 24 and, optionally, an airflow sensor 26 are provided within the cylindrical hollow tube power supply portion 14. The battery 22 is electrically connected to the control electronics 24, which are electrically connected to the LED 18 and the airflow sensor 26. In this example, the LED 18 is at the front end of the power supply portion 14, adjacent to the end cap 12; and the control electronics 24 and airflow sensor 26 are provided in the central cavity at the other end of the battery 22 adjacent the atomizer/liquid reservoir portion 16.

The airflow sensor 26 acts as a puff detector, detecting a user puffing or sucking on the atomizer/liquid reservoir portion 16 of the e-cigarette 10. The airflow sensor 26 can be any suitable sensor for detecting changes in airflow or air pressure, such as a microphone switch including a deformable membrane which is caused to move by variations in air pressure. Alternatively, the sensor may be, for example, a Hall element or an electro-mechanical sensor.

The control electronics 24 are also connected to an atomizer 28. In the example shown, the atomizer 28 includes a heating coil 30 which is wrapped around a wick 32 extending across a central passage 34 of the atomizer/liquid reservoir portion 16. The central passage 34 may, for example, be defined by one or more walls of the liquid reservoir and/or one or more walls of the atomizer/liquid reservoir portion 16 of the e-cigarette 10. The coil 30 may be positioned anywhere in the atomizer 28 and may be transverse or parallel to a longitudinal axis of a cylindrical liquid reservoir 36. The wick 32 and heating coil 30 do not completely block the central passage 34. Rather an air gap is provided on either side of the heating coil 30 enabling air to flow past the heating coil 30 and the wick 32. The atomizer may alternatively use other forms of heating elements, such as ceramic heaters, or fiber or mesh material heaters. Nonresistance heating elements such as sonic, piezo, and jet spray may also be used in the atomizer in place of the heating coil.

The central passage 34 is surrounded by the cylindrical liquid reservoir 36 with the ends of the wick 32 abutting or extending into the liquid reservoir 36. The wick 32 may be a porous material such as a bundle of fiberglass fibers or cotton or bamboo yarn, with liquid in the liquid reservoir 36 drawn by capillary action from the ends of the wick 32 towards the central portion of the wick 32 encircled by the heating coil 30.

The liquid reservoir 36 may alternatively include wadding (not shown in FIG. 1) soaked in liquid which encircles the central passage 34 with the ends of the wick 32 abutting the wadding. In other embodiments, the liquid reservoir may comprise a toroidal cavity arranged to be filled with liquid and with the ends of the wick 32 extending into the toroidal cavity.

An air inhalation port 38 is provided at the back end of the atomizer/liquid reservoir portion 16 remote from the end cap 12. The inhalation port 38 may be formed from the cylindrical hollow tube atomizer/liquid reservoir portion 16 or may be formed in an end cap.

In use, a user sucks on the e-cigarette 10. This causes air to be drawn into the e-cigarette 10 via one or more air inlets, such as air inlets 20, and to be drawn through the central passage 34 towards the air inhalation port 38. The change in air pressure which arises is detected by the airflow sensor 26, which generates an electrical signal that is passed to the control electronics 24. In response to the signal, the control electronics 24 activate the heating coil 30, which causes liquid present in the wick 32 to be vaporized creating an aerosol (which may comprise gaseous and liquid components) within the central passage 34. As the user continues to suck on the e-cigarette 10, this aerosol is drawn through the central passage 34 and inhaled by the user. At the same time, the control electronics 24 also activate the LED 18 causing the LED 18 to light up, which is visible via the translucent end cap 12. Activation of the LED may mimic the appearance of a glowing ember at the end of a conventional cigarette. As liquid present in the wick 32 is converted into an aerosol, more liquid is drawn into the wick 32 from the liquid reservoir 36 by capillary action and thus is available to be converted into an aerosol through subsequent activation of the heating coil 30.

Some e-cigarette are intended to be disposable and the electric power in the battery 22 is intended to be sufficient to vaporize the liquid contained within the liquid reservoir 36, after which the e-cigarette 10 is thrown away. In other embodiments, the battery 22 is rechargeable and the liquid reservoir 36 is refillable. In the cases where the liquid reservoir 36 is a toroidal cavity, this may be achieved by refilling the liquid reservoir 36 via a refill port (not shown in FIG. 1). In other embodiments, the atomizer/liquid reservoir portion 16 of the e-cigarette 10 is detachable from the power supply portion 14 and a new atomizer/liquid reservoir portion 16 can be fitted with a new liquid reservoir 36 thereby replenishing the supply of liquid. In some cases, replacing the liquid reservoir 36 may involve replacement of the heating coil 30 and the wick 32 along with the replacement of the liquid reservoir 36. A replaceable unit comprising the atomizer 28 and the liquid reservoir 36 may be referred to as a cartomizer.

The new liquid reservoir may be in the form of a cartridge (not shown in FIG. 1) defining a passage (or multiple passages) through which a user inhales aerosol. In other embodiments, the aerosol may flow around the exterior of the cartridge to the air inhalation port 38.

Of course, in addition to the above description of the structure and function of a typical e-cigarette 10, variations also exist. For example, the LED 18 may be omitted. The airflow sensor 26 may be placed, for example, adjacent to the end cap 12 rather than in the middle of the e-cigarette. The airflow sensor 26 may be replaced by, or supplemented with, a switch which enables a user to activate the e-cigarette manually rather than in response to the detection of a change in airflow or air pressure.

Different types of atomizers may be used. Thus, for example, the atomizer may have a heating coil in a cavity in the interior of a porous body soaked in liquid. In this design, aerosol is generated by evaporating the liquid within the porous body either by activation of the coil heating the porous body or alternatively by the heated air passing over or through the porous body. Alternatively the atomizer may use a piezoelectric atomizer to create an aerosol either in combination or in the absence of a heater.

Figure 2A:
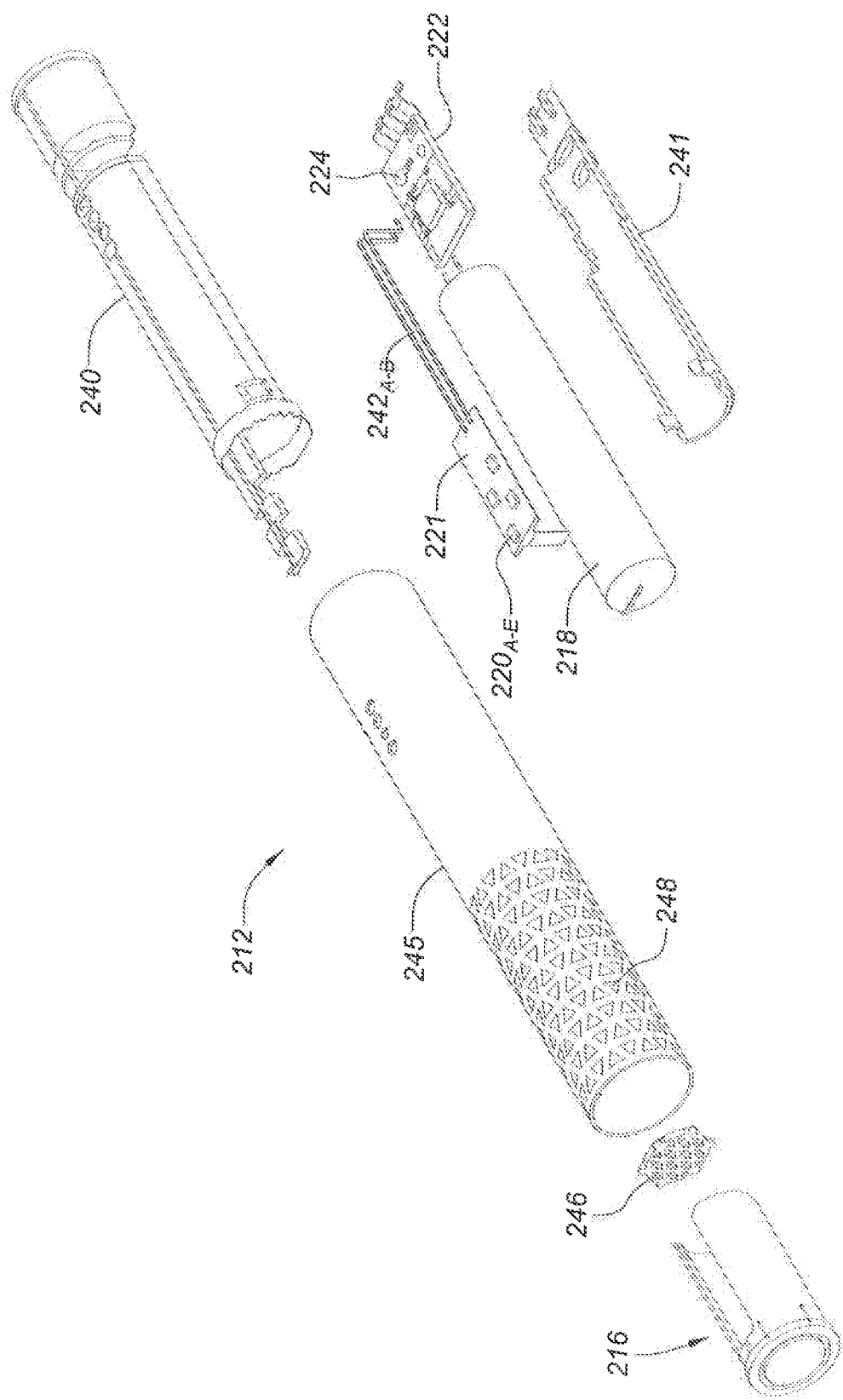
FIG. 2A is a partial exploded assembly view of an eCig battery housing, consistent with various aspects of the present disclosure.

FIG. 2A is a partial exploded assembly view of an eCig power supply portion 212 (also referred to as a power supply portion), consistent with various aspects of the present disclosure. The power supply portion 212 houses a number of electrical components that facilitate the re-charging and re-use of the power supply portion 212 with disposable and refillable atomizer/liquid reservoir portions (14 as shown in FIG. 1), which are also referred to as atomizer/liquid reservoir portions. A battery 218 is electrically coupled to controller circuitry 222 on a printed circuit board. An airflow sensor 224 for determining one or more characteristics of a user's draw from the eCig is also located on the printed circuit board, and communicatively coupled to the controller circuitry 222. In various embodiments consistent with the present disclosure, the airflow sensor 224 may be a mass airflow sensor, a pressure sensor, a velocity sensor, a heater coil temperature sensor, or any other sensor that may capture relevant draw characteristics (either directly or through indirect correlations). In the present embodiment, the airflow sensor 224 is a mass airflow sensor that determines the flow of air across the airflow sensor 224. The measured flow of air is then drawn through the atomizer/liquid reservoir portion, where heater coils atomize eCig juice into the air, and into a user's mouth. Accordingly, by measuring the mass flow rate of air through the power supply portion 212, the controller circuitry 222 may adjust a heating profile of a heating coil in a atomizer/liquid reservoir portion (e.g., power, length of time, etc.), as well as provide a variable indication of the strength of the draw—by way of LEDs $220_{A-E}$, which may be independently addressed by the controller circuitry or powered at varying intensities to indicate characteristics indicative of the eCig's functionality. For example, varying the illumination intensity based on the sensed mass airflow. In further embodiments, the LEDs may also indicate other functional aspects of the eCig, such as remaining battery life, charging, sleep mode, among others.

In various embodiments of the present disclosure, electrical pins extending from the printed circuit board may be electrically coupled to a atomizer/liquid reservoir portion, and thereby allow for both energy transfer and data communication between the power supply portion 212 and the atomizer/liquid reservoir portion (not shown). In various other embodiments, pins may extend from a surface of the printed circuit board to an exterior of the power supply portion to facilitate charging and data communication with external circuitry.

To provide user indications of status, power remaining, use, error messages, among other relevant information, a flexible printed circuit board 221 is communicatively coupled to controller circuitry 222 via wire leads $242_{A-B}$. The flexible circuit board 221 may include one or more light sources. In the present embodiment, the flexible circuit board 221 includes LEDs $220_{A-E}$. When assembled into the rest of the power supply portion 212, the LEDs $220_{A-E}$ both illuminate a circumferential portion of light guide 216, and a tip diffuser 246 that illuminates a distal end of the light guide 216. The tip diffuser 246 and the light guide 216 together facilitate even illumination of the distal end of the power supply portion 212 in response to the activation of the LEDs $220_{A-E}$.

As shown in FIG. 2A, once electrically coupled to one another (e.g., by solder), battery 218, flexible printed circuit board 221, and a printed circuit board containing controller circuitry 222 and airflow sensor 224 are encased by upper sub-assembly housing 240 and lower sub-assembly housing 241. In one embodiment, the upper sub-assembly housing 240 and the lower sub-assembly housing 241 can create a flow channel. The flow channel created by the upper sub-assembly housing 240 and the lower sub-assembly housing 241 can direct airflow over the airflow sensor. The sub-assembly housing portions positively locate the various components with the sub-assembly. In many embodiments, the sub-assembly housing portions utilize locating pins and integral locking features to maintain the sub-assembly after assembly.

Once assembly is complete on the sub-assembly, the sub-assembly may be slid into tube 245 from one end, and tip diffuser 246 and circumferential light guide 216 may be inserted from the opposite end of the tube to complete assembly of power supply portion 212. By way of the distal tip of the circumferential light guide 216 and etch pattern 248 in tube 245, LEDs $220_{A-E}$ may illuminate evenly around a distal circumferential portion of the tube 245, and a distal tip of the power supply portion 212.

In various embodiments of the present disclosure, one or more keying features may be present on an exterior surface of upper and/or lower sub-assembly housing portions 240 and 241. When the sub-assembly is inserted into tube 245, mating keying features along an inner surface of the tube 245 rotationally align the tube and the sub-assembly along a longitudinal axis and prevent the sub-assembly from spinning therein.

The use of a sub-assembly during manufacturing helps minimize assembly complexity, as well as reduce overall assembly time. Moreover, the sub-assembly helps to mitigate scrap as the sub-assembly allows for rapid re-work of a power supply portion 212, such as when electronic circuitry within the power supply portion fails in testing. Moreover, the sub-assembly helps to mitigate common failure modes of eCigs during its useful life by reducing shock and vibration related damage to the sub-components. Specifically, by positively locating controller circuitry 222 and flexible circuit board 221 within the upper and lower sub-assembly housing portions 240 and 241, wire leads $242_{A-B}$ and bonding pads electrically coupling the circuitry are less likely to experience failure modes. For example, stress fractures at a solder joint on a bonding pad.

In various embodiments of the present disclosure, pattern 248 on tube 245 may include various different patterns, shapes, images and/or logos. In the present embodiment, the pattern 248 is a plurality of triangles positioned in proximity to one another. The pattern 248 may be laser etched onto a painted surface of the tube 245, silk screened, drilled or otherwise cut into an outer surface of the tube 245, and/or the tube itself can be translucent or semi-translucent and the pattern may be disposed on an outer surface 350 of circumferential light guide 316. The pattern 248 on an outer surface of tube 245 allows controller circuitry 222 to provide visual indications of the eCigs functionality via light being emitted from LEDs $220_{A-E}$ through circumferential light guide 216. The eCig may provide a plurality of visual indications by varying the brightness (e.g., LED duty cycle), color (e.g., output frequency and/or multi-diode LEDs), location, on/off time, patterning, among other visually distinguishable characteristics.

Figure 2B:
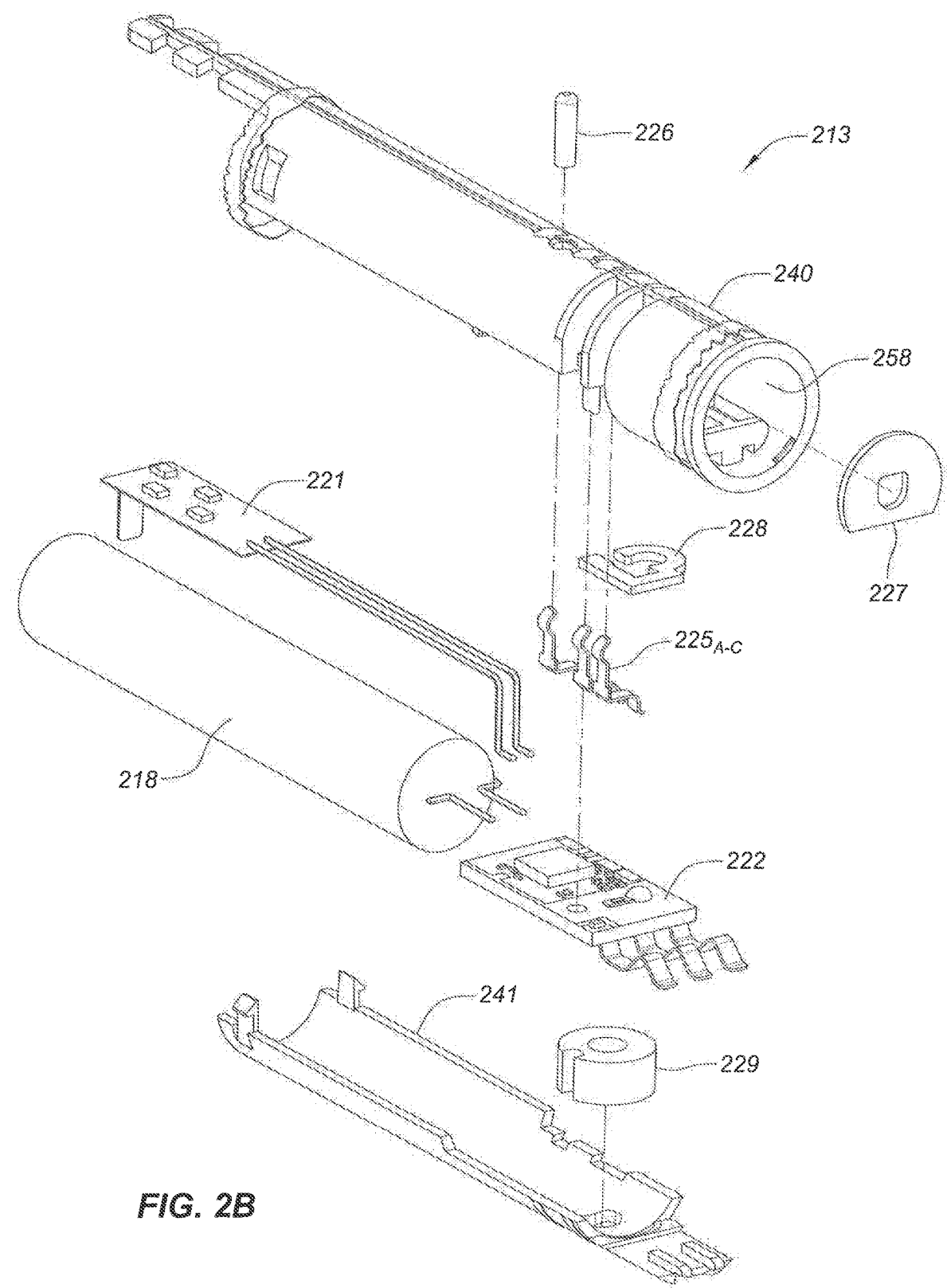
FIG. 2B is a partial exploded assembly view of an eCig battery housing, consistent with various aspects of the present disclosure.

FIG. 2B is a partial exploded assembly view of an eCig power supply portion sub-assembly 213, consistent with various aspects of the present disclosure. As shown in FIG. 2B, flex circuit 221 and battery 218 are electrically coupled to controller circuitry 222 via wire leads which are soldered on to the controller circuitry. Contacts $225_{A-C}$ (also referred to as electrical pins) are also electrically coupled to the controller circuitry 222 and extend toward apertures within the upper sub-assembly housing 240. The contacts $225_{A-C}$ facilitate electrical communication between the controller circuitry 222 and an external circuit, as well as charging the battery 218.

When assembled, flex circuit 221 extends over and around battery 218. The battery being circumferentially enclosed by upper and lower sub-assembly housing portions 240 and 241. Controller circuitry 222 is sandwiched between spacer 229 and MAF gasket 228; the spacer and MAF gasket contacting respective surfaces of upper and lower sub-assembly housing portions 240 and 241 and thereby positively locate the controller circuitry within the sub-assembly. The spacer 229 includes an inner aperture that functions as a light guide to deliver light from an LED on the controller circuitry 222 through an aperture within the lower sub-assembly housing 241. The MAF gasket 228 facilitates an airflow passage between the controller circuitry 222 and the upper sub-assembly housing 240. The MAF gasket 228 both forms a seal between the controller circuitry 222 and the upper sub-assembly housing to direct the airflow past the airflow sensor 224 (as shown in FIG. 2A), as well as to maintain a desired cross-sectional area of the airflow passage in the vicinity of a mass airflow sensor.

Female connector port 258 mates to a male connector port on a atomizer/liquid reservoir portion of the eCig, and provides a flow of air via a fluid outlet, and power and data communication signals via a plurality of electrical contacts that are communicatively coupled to corresponding electrical contacts on the male connector port (when the male and female connector ports are mated to one another). In various embodiments of the present disclosure, the male and female connector ports are hemicylindrical in shape. As used herein, "hemicylindrical" describes parts having the shape of a half a cylinder, as well as parts that include a larger or smaller portion of a cylinder when cut by a plane that is parallel to the longitudinal axis (or lengthwise) of the cylinder. An airflow gasket 227 is inserted into the female connector port 258 and facilitates a fluid seal with the mating male connector port. In one particular embodiment, airflow sensor 224 is a mass airflow sensor that measures a flow of air through the eCig, the airflow gasket 227 prevents additional air from entering the airflow into the atomizer/liquid reservoir portion (or the escape of air from the airflow) after the mass airflow sensor has measured the airflow.

Once the sub-assembly 213 has been assembled and inserted into an outer tube 245, a locking pin 226 is inserted through corresponding apertures in the outer tube and the upper sub-assembly housing 240 to axially and rotationally couple the sub-assembly 213 within the power supply portion 212.

Figure 3:
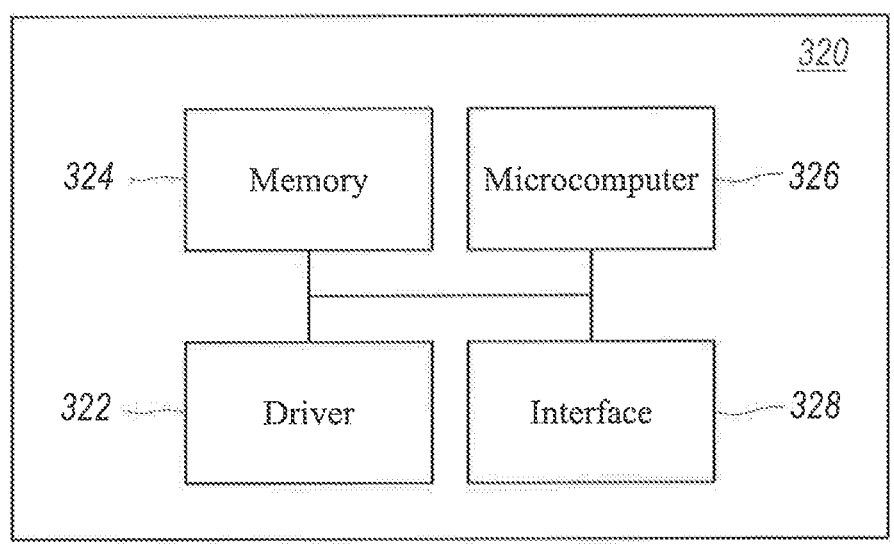
FIG. 3 is an example of a microcontroller that is constructed according to an aspect of the disclosure.

FIG. 3 shows an example of the microcontroller 320 constructed according to an aspect of the disclosure. The microcontroller 320 comprises a microcomputer 326, a memory 324 and an interface 328. The microcontroller 320 can include a driver 322 that drives an atomizer (not shown). The driver 322 can include, e.g., a pulse-width modulator (PWM) or signal generator. The microcomputer 320 is configured to execute a computer program, which can be stored externally or in the memory 324, to control operations of the eCig, including activation (and deactivation) of the heating element. The memory 324 includes a computer-readable medium that can store one or more segments or sections of computer code to carry out the processes described in the instant disclosure. Alternatively (or additionally) code segments or code sections may be provide on an external computer-readable medium (not shown) that may be accessed through the interface 328.

It is noted that the microcontroller 320 may include an application specific integrated circuit (IC), or the like, in lieu of the microcomputer 326, driver 322, memory 324, and/or interface 328.

The microcontroller may be configured to log medium flow data, including mass flow, volume flow, velocity data, time data, date data, flow duration data, and the like, that are associated with the medium flow. The medium may comprise an aerosol, a gas (e.g., air), a liquid, or the like. The microcontroller may be configured not only to turn ON/OFF a heater based on such data, but to also adjust control parameters such as heater PWM or amount of liquid solution dispensed onto a heating surface. This control may be done proportionally to the flow data or according to an algorithm where flow data is a parameter. In addition, the microcontroller may use flow data to determine flow direction and restrict or limit false activation of the heater in case the user accidentally blows into the eCig.

Figure 4:
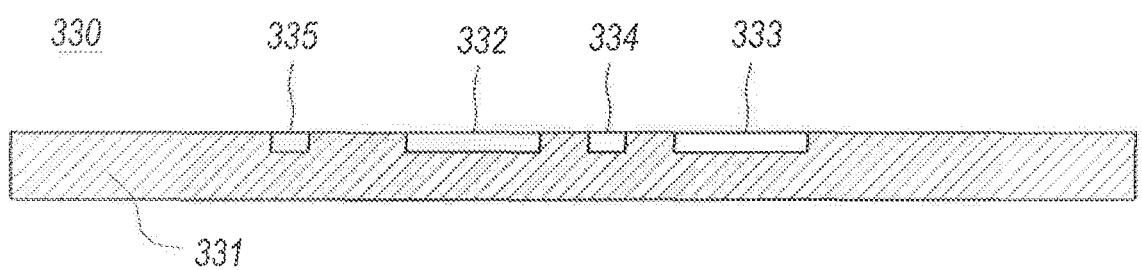
FIG. 4 is an example of a flow sensor that is constructed according to an aspect of the disclosure.

FIG. 4 shows an example of a flow sensor 330 that is constructed according to an aspect of the disclosure. The flow sensor 330 comprises a substrate 331 and a thermopile (e.g., two or more thermocouples), including an upstream thermopile (or thermocouple) 332 and a downstream thermopile (or thermocouple) 333. The substrate 331 may include a thermal isolation base. The flow sensor 130 may comprise a heater element 334. The flow sensor 330 may comprise a reference element 335. The heater element 334 may include a heater resistor. The reference element 335 may include a reference resistor.

As seen in FIG. 4, the thermopiles 332, 333 may be symmetrically positioned upstream and downstream from the heater element 334. The heater element 334 heats up the hot junctions of the thermopiles 332, 333. In response, each of the thermopiles 332, 333 generates an output voltage that is proportional to the temperature gradient between its hot and cold junctions (the "Seebeck" effect). The hot junctions of the thermopiles 332, 333 and the heater element 334 may reside on the thermal isolation base. Mass airflow sensor signal conditioning may be composed of various forms of filters or gain amplifiers. Filters may be used to eliminate noise before or after signal amplification, thereby reducing sensitivity to unwanted environmental noises or pressure changes. Filtering can be accomplished using low pass, high pass, band pass, or a combination thereof. Signal gain amplification may be accomplished by employing electronic amplification on the upstream or downstream thermopile signals, or a combination thereof. Amplification of upstream or downstream thermopile signals may use a single state or multiple cascaded stages for each signal, or combination of these signals to form a sum or difference. The amplifier circuit may include means to introducing a signal offset. The amplifier may include transistors, operational amplifiers, or other integrated circuits.

Figure 5A:
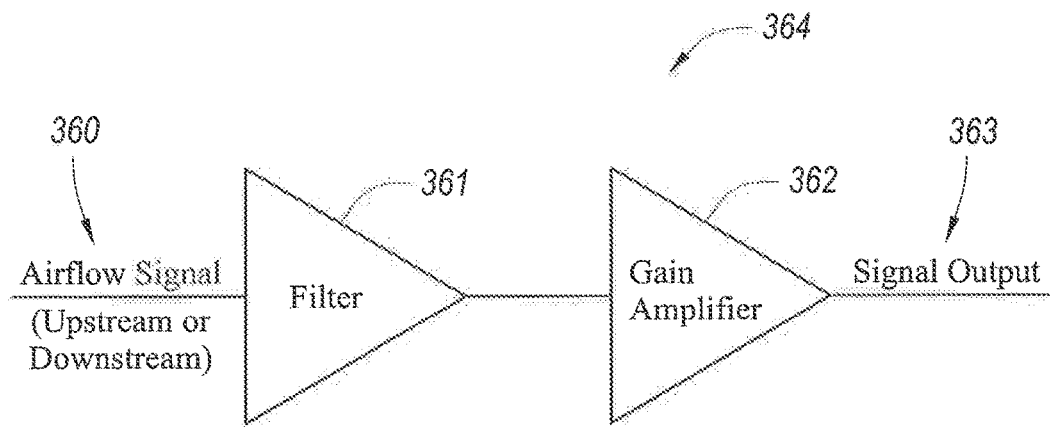
FIGS. 5A and 5B are examples of signal amplification and filtering through a single amplifier or multiple amplifiers.
Figure 5B:
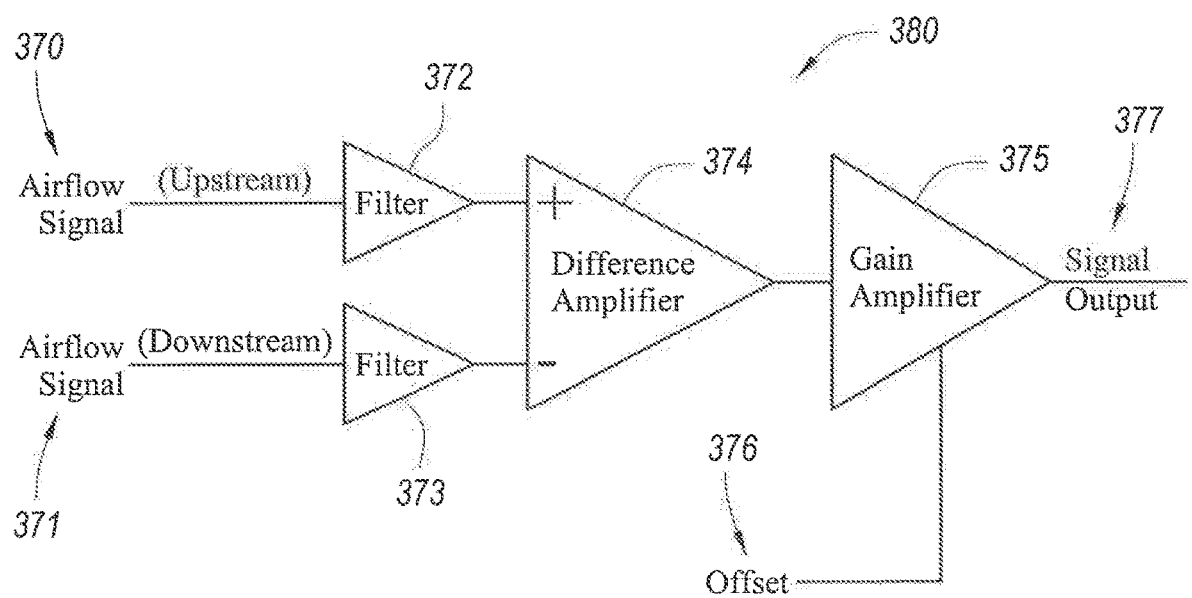

FIGS. 5A and 5B illustrate an example of a single amplifier with a filter 364 and a difference amplifier and filters for upstream and downstream, with offset 380. As shown in the single amplifier with a filter 364 in FIG. 5A, the airflow signal 360 passes through a filter 361 and a gain amplifier 362 before a signal output 363 is transmitted. The difference amplifier and filters for upstream and downstream, with offset 380 shown in FIG. 5B comprises an upstream airflow signal 370 and a downstream airflow signal 371. The upstream airflow signal 370 passes through a first filter 372 and the downstream airflow signal passes through a second filter 373. The outputs of the first and second filters 371,372 then enter a difference amplifier 374. A signal is then output from the difference amplifier 374 and enters a gain amplifier 375 along with an offset 375. The gain amplifier 376 then outputs a signal output 377.

Figure 6:
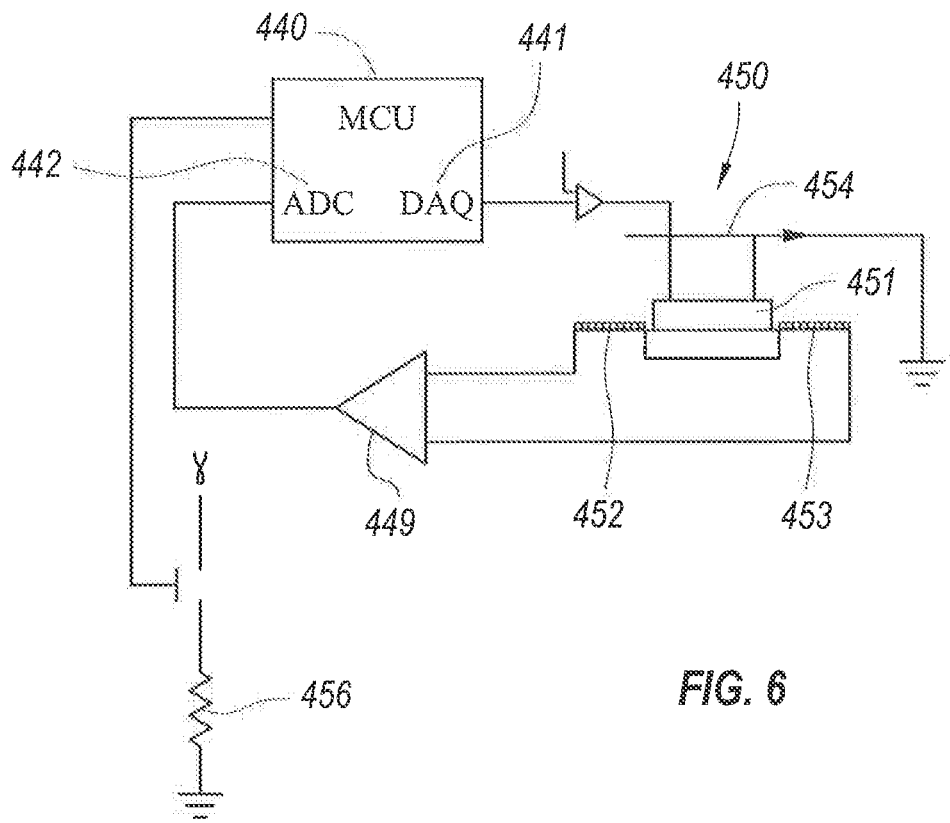
FIG. 6 is an electrical diagram of an eCig comprising a first and second thermopile.

FIG. 6 illustrates an electrical diagram of an embodiment of the disclosure comprising a first thermopile 452 and a second thermopile 453. The eCig depicted in FIG. 6 comprises a microcontroller 440, a mass airflow sensor 450, an amplifier 449, and a heater 456. The mass airflow sensor 450 comprises a mass airflow heater 451, a first thermopile 452, and a second thermopile 453. The electrical diagram further illustrates the direction of airflow 454 over the mass airflow heater 451 and the first and second thermopiles 452, 453. The microcontroller 440 can comprise a data acquisition circuit 441, and an analog-to-digital converter 442. The data acquisition circuit 441 can log and transmit data such as temperature of the heater 456, the number of times the heater 456 has been activated in a certain time, the length of time the heater 456 had been activated, and other information. A more detailed description of data acquisition and transmission can be found in commonly assigned U.S. Provisional Application No. 61/907,239 filed 21 Nov. 2013, the entire disclosure of which is hereby incorporated by reference as though fully set forth herein. The analog-to-digital converter 442 can output information about the eCig to the microcontroller 440, the data acquisition circuit 441, and other devices and sensors that may be present on the microcontroller 440 or otherwise connected to the eCig.

Figure 7:
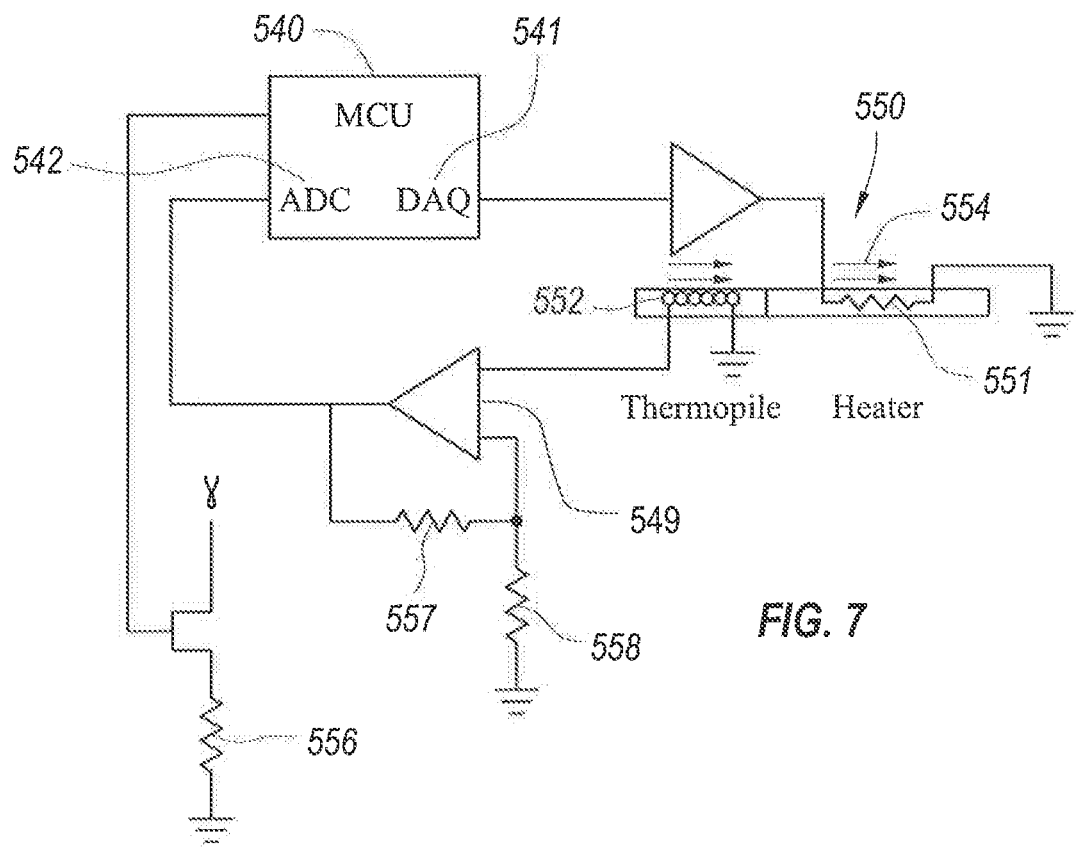
FIG. 7 is an electrical diagram of an eCig comprising one thermopile.

FIG. 7 illustrates an electrical diagram of another embodiment of the disclosure comprising one thermopile 552. The eCig depicted in FIG. 7 comprises a microcontroller 540, a mass airflow sensor 550, an amplifier 549, and a heater 556. The mass airflow sensor 550 comprises a mass airflow heater 551 and a thermopile 552. The electrical diagram further illustrates the direction of airflow over the heater 554 and the thermopile 552. The microcontroller 540 can comprise a data acquisition circuit 541, and an analog-to-digital converter 542. The data acquisition circuit 541 can log and transmit data such as temperature of the heater 556, the number of times the heater 556 has been activated in a certain time, the length of time the heater 556 had been activated, and other information. The analog-to-digital converter 542 can output information about the eCig to the microcontroller 540, the data acquisition circuit 541, and other devices and sensors that may be present on the microcontroller 540 or otherwise connected to the eCig. In one embodiment, the eCig can also comprise feedback and gain resistors 557, 558. More information regarding the airflow sensor can be found in PCT Publication no. WO 2014/205263, filed 19 Jun. 2014, which is incorporated by reference herein as though set forth in its entirety.

Figure 8A:
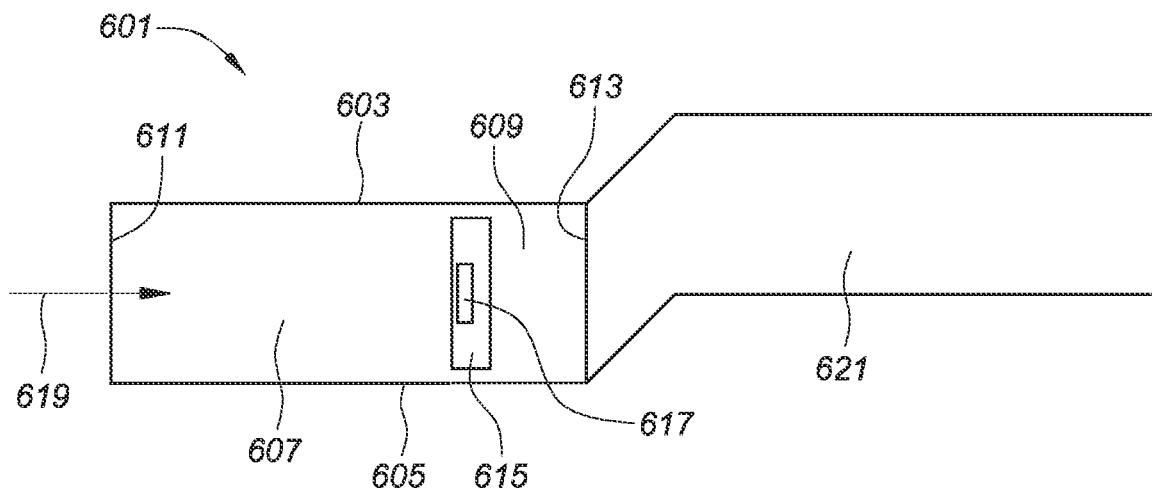
FIGS. 8A and 8B are an example of a flow channel according to the principles of the disclosure.
Figure 8B:
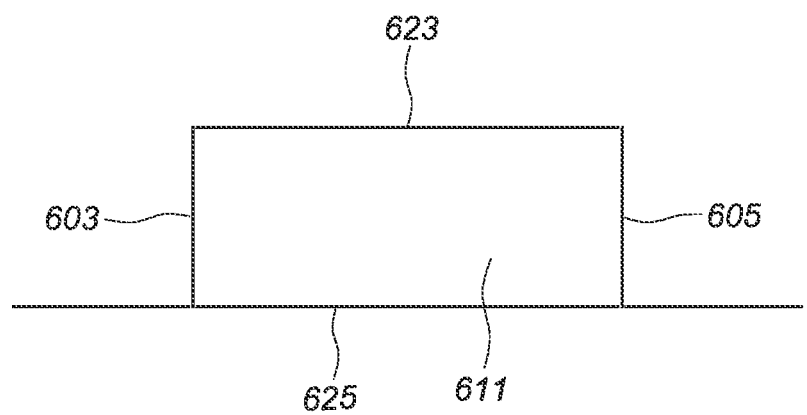

FIGS. 8A and 8B show an example of a flow channel according to the principles of the disclosure. As seen in FIGS. 8A and 8B, the flow channel can be shaped in the vicinity of the sensor so as to direct a majority of flow over the sensing surface, thus increasing the sensitivity of the system. FIG. 8A depicts a top down view of one embodiment of a flow channel 601. FIG. 8B depicts an end view of the flow channel 601 shown in FIG. 8A. The flow channel 601 comprises a first side wall 603, a second side wall 605, a top wall 623, a bottom wall 625, an incoming airflow opening 611, an incoming airflow pathway 607, a sensor assembly 615, an outgoing airflow pathway 609, and an outgoing airflow opening 613. The first side wall 603, the second side wall 605, the top wall 623, and the bottom wall 625 define the incoming airflow opening 611, the incoming airflow pathway 607, the outgoing airflow pathway 609, and the outgoing airflow opening 613. The incoming airflow opening 611 can allow air to enter the flow channel 601. The incoming airflow pathway 607 can extend along a longitudinal axis of the flow channel 601. The incoming airflow pathway 607 can extend a distance along the longitudinal axis and comprise enough volume so that any air entering the flow channel 601 through the incoming airflow opening 611 creates a laminar flow before passing over the sensor assembly 615. In one embodiment, to achieve a laminar flow over the sensor assembly, the incoming airflow pathway can comprise a longitudinal length of 1.5-2 mm. In other embodiments, the longitudinal length of the incoming airflow pathway can be adjusted in response to different dimensions and volumes of the flow channel. The sensitivity of the sensor assembly 615 can be increased by decreasing the volume of the flow channel 601. However, by decreasing the volume of the flow channel 601 a draw resistance for a user is increased. As the volume of the flow channel 601 increases the signal quality decreases, but the draw resistance is decreased. After the air has passed over the sensor assembly 615, the airflow can be turbulent as it passes through the rest of the system. The sensor assembly 615 can comprise a sensor 617. The sensor 617 can detect an airflow over the sensor assembly 615 and can further detect a mass of airflow over the sensor assembly 615 and passing through the flow channel 601. The airflow can move over the sensor along the airflow path 619 In one embodiment, the sensor can comprise a mass airflow sensor. In another embodiment, the sensor can comprise a capacitive sensor. After passing over the sensor assembly 615, an airflow through the flow channel 601 can enter the outgoing airflow pathway 609 and exit the flow channel 601 through the outgoing airflow opening 613. After leaving the flow channel 601, the airflow can enter an external airflow pathway 621. In one embodiment, the external airflow pathway 621 can be sealed such that any air entering the flow channel 601 and passing over the sensor assembly 615 can be routed through the flow channel 601 and the external airflow pathway 621 to an atomizer (not shown).

In other embodiments, a diverter can be present after the airflow has passed over the sensor assembly such that a portion of the air passes over the atomizer and a portion of the air diverts around the atomizer. In these embodiments, the electronic smoking device is configured to, at least in part, pass the airflow over the atomizer. In one embodiment, the portion of air that passes over the atomizer can be 50% or greater of the air that passes over the sensor assembly. In another embodiment, the portion of air that passes over the atomizer can be 50% or less of the air that passes over the sensor assembly. By diverting a portion of the airflow that passes over the sensor assembly, the amount of air that passes over the atomizer can be controlled and the amount of aerosol or vapor created by the atomizer can be regulated. In yet other embodiments, an additional air inlet can be added downstream of the sensor assembly, such that additional air can be added to the airflow that has passed over the sensor assembly. In one embodiment, adding an additional air inlet downstream of the sensor assembly can decrease the sensitivity of the sensor signal, but can further dilute the vapor stream. In yet other embodiments, additional components can be added to divert or add airflow to the airflow stream after it has passed the sensor assembly. The additional components can be used to divert the airflow stream away from the atomizer, add additional air to the airflow stream, or impart additional airflow after the airflow stream has passed the atomizer. In yet other embodiments, the airflow passing over the sensor assembly can comprise a first portion of the airflow passing through a downstream portion of the electronic smoking device. A second portion of the airflow passing through an upstream portion of the electronic smoking device can be diverted around the sensor assembly. In one embodiment, the second portion of the airflow can join with the first portion of the airflow after the first portion of the airflow has passed over the sensor assembly. In one embodiment, the atomizer can comprise a heater. In other embodiments, the atomizer can comprise a mechanical or thermal atomizer as would be known to one in the art. In one embodiment, the flow channel can be defined by the foam and plastic portions of the battery housing as illustrated in FIGS. 2A and 2B. In one embodiment, the foam portion of the flow channel can comprise a minimum compression ratio of 30%. When foam is used within the flow channel, the foam can be compressed enough to keep the flow channel sealed, but not compressed to an extent that the foam intrudes into the channel. In one embodiment, the foam can comprise a micro closed-seal foam.

Figure 9:
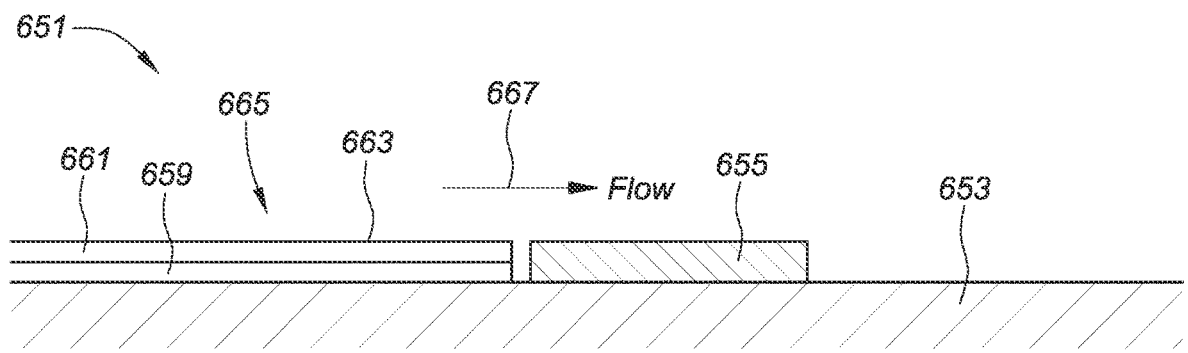
FIG. 9 is a side view of one embodiment of a sensor assembly.

FIG. 9 illustrates a side view of one embodiment of a sensor assembly 651. The sensor assembly 651 can comprise a support structure 653, a sensor 655, a first layer 659, and a second layer 661. The support structure 653 can comprise a PCB or other component that can be electrically coupled to the sensor 655. The sensor 655 can detect an airflow over the sensor assembly 651 and can further detect a mass of airflow over the sensor assembly 651. In one embodiment, the sensor can comprise a mass airflow sensor. In another embodiment, the sensor can comprise a capacitive sensor. The first layer 659 and the second layer 661 can be used to create an upper surface 663 that extends along an incoming portion 665 of the sensor assembly 651. The upper surface 663 can comprise a height above the support structure 653 similar to the height the sensor 655 extends above the support structure 653. The upper surface 663 created by the first layer 659 and the second layer 661 can be used to minimize turbulence created by an airflow passing through an airflow pathway 667 and over the sensor assembly 651. The first layer 659 can comprise any one of a number of substances that can be used during a PCB manufacturing process. In one embodiment, the first layer 659 can comprise copper. In other embodiments, the first layer 659 can comprise solder mask, silkscreen, or any other material that can be deposited on a PCB or other support structure. The second layer 661 can comprise any one of a number of substances that can be used during a PCB manufacturing process. In one embodiment, the second layer 661 can comprise solder mask. In other embodiments, the second layer 661 can comprise copper, silkscreen, or any other material that can be deposited on a PCB or other support structure. In one embodiment, a silkscreen layer can be further deposited on top of the second layer 661. These materials can be used during the manufacturing of the sensor assembly 651. Using materials already present during the manufacture of a PCB component, additional manufacturing costs can be limited. In one embodiment, the sensor can be formed and then a backgrinding process can be used to remove portions of the sensor that are not integral to the sensor. By backgrinding the sensor, the height of the sensor can be decreased, requiring less additional material to be placed on the support structure. In one embodiment, after undergoing the backgrinding process the sensor can comprise a height of 0.1 mm. In another embodiment, after undergoing the backgrinding process the sensor can comprise a height of 0.2 mm.

Figure 10:
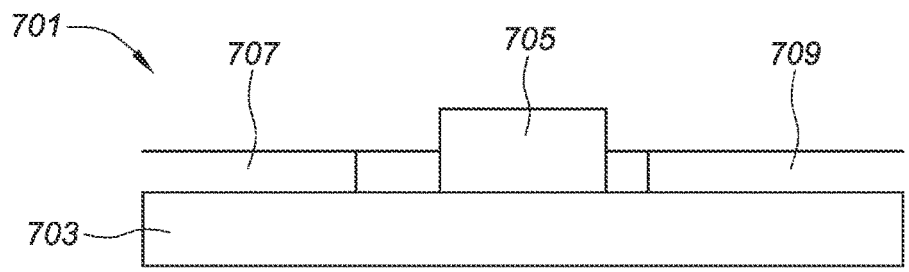
FIG. 10 is a schematic view of another embodiment of a sensor assembly.

FIG. 10 depicts a schematic view of another embodiment of a sensor assembly 701. The sensor assembly 701 can comprise a support structure 703, a sensor 705, a first structure component 707, and a second structure component 709. The sensor 705 can be coupled to the support structure 703. In one embodiment, the sensor 705 can be electrically coupled to the support structure 703. The first structure component 707 and the second structure component 709 can be coupled to the support structure 703. The first structure component 707 and the second structure component 709 can assist in securing the sensor 705 to the support structure 703. In another embodiment, the first structure component 707 and the second structure component 709 can each comprise an upper surface adjacent to an upper surface of the sensor 705. The first support structure 707 and the second support structure 709 can be used to assist in directing an airflow over the sensor 705 and to minimize air currents that could be disruptive or otherwise unwanted when air is passed over the sensor 705.

Figure 11A:
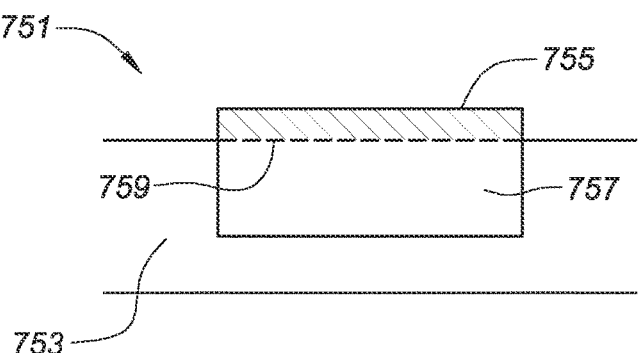
FIG. 11A is a schematic view of another embodiment of a sensor assembly.

FIG. 11A illustrates another embodiment of a sensor assembly 751. The sensor assembly 751 can comprise a support structure 753, a sensor base portion 757, a sensor top portion 755, and a sensor transition region 759. The support structure 753 can comprise a depression sized and configured to house the sensor base portion 757. When the sensor base portion 757 is placed within the depression of the support structure 753, the sensor top portion 755 can be above an upper portion of the support structure. The sensor transition region 759 can be lined up with an upper surface of the support structure 753. By securing the sensor base portion 757 within a depression of the support structure 753, the sensor top portion 755 can minimize any effects of the sensor top portion 755 on airflow flowing past the sensor assembly 751. As stated above, in other embodiments, additional material can be placed on the support structure to further minimize any effects, turbulence or otherwise, possibly caused on an airflow passing over the sensor assembly 751.

Figure 11B:
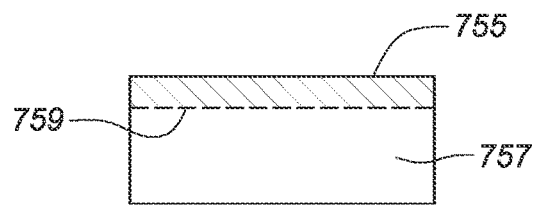
FIG. 11B is a schematic view of an embodiment of a sensor.

FIG. 11B illustrates the sensor of FIG. 11A. The sensor comprises the sensor base portion 757, the sensor top portion 755, and the sensor transition region 759. As described above, the sensor base portion 757 can be placed within a depression in a support structure. In other embodiments, the sensor base portion 757 can be coupled to a top surface of a support structure. The sensor top portion 755 can comprise the portion of the sensor that is needed to interact with an airflow passing over the sensor to measure an airflow rate. In one embodiment, the sensor transition region 759 can be denoted as separating the portion of the sensor that needs to be exposed to a passing airflow (the sensor top portion 755) and the portion of the sensor that does not need to be exposed to a passing airflow (the sensor bottom portion 757).

Figure 12A:
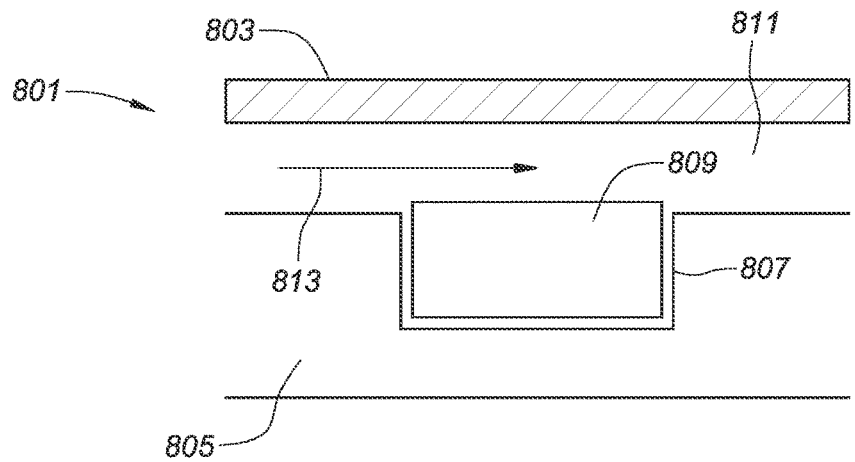
FIGS. 12A-12C are schematics of several embodiments of flow channels according to the disclosure.

FIG. 12A depicts a schematic view of one embodiment of a flow channel 801. The flow channel 801 can comprise an upper housing 803, a support structure 805, a support depression 807, a sensor 809, and an airflow pathway 811. The upper housing 803, the support structure 805, and the sensor 809 can define the airflow pathway 811. Air entering the flow channel 801 can pass over the sensor 809 in the airflow direction 813. The support depression 807 can be sized and configured to house a lower portion of the sensor 809. When the lower portion of the sensor 809 is placed within the support depression 807, an upper portion of the sensor 809 can be above an upper surface of the support structure 805. By securing the sensor 809 within the support depression 807, the sensor 809 can minimize any effects on airflow flowing past the sensor 809. As stated above, in other embodiments, additional material can be placed on the support structure to further minimize any effects, turbulence or otherwise, possibly caused on an airflow passing over the sensor 809. The upper housing can comprise a variety of materials. In one embodiment, the upper housing can comprise plastic. In another embodiment, the upper housing can comprise tape placed over the flow channel. In yet other embodiments, the upper housing can comprise any other material that can withstand deformation from air flowing through the airflow pathway.

Figure 12B:
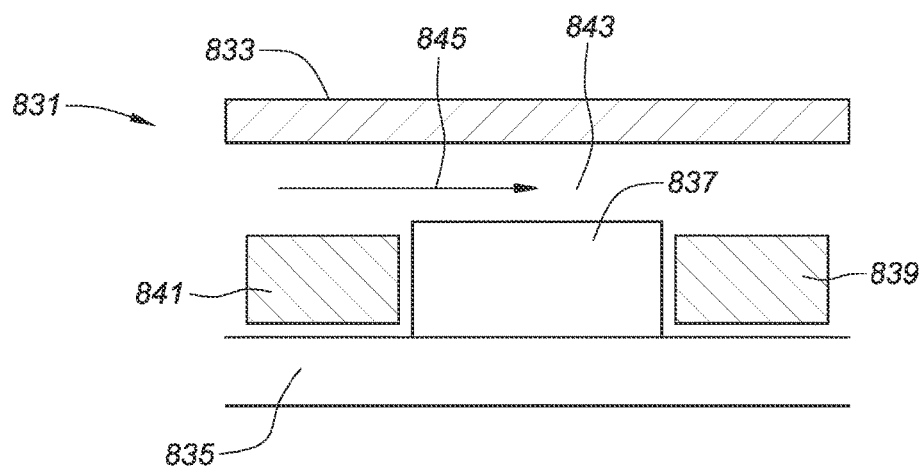

FIG. 12B depicts a schematic view of another embodiment of a flow channel 831. The flow channel 831 can comprise an upper housing 833, a support structure 835, a sensor 837, a first structure component 841, a second structure component 839, and an airflow pathway 843. The upper housing 833, the support structure 835, the first structure component 841, the second structure component 839, and the sensor 837 can define the airflow pathway 843. Air entering the flow channel 831 can pass over the sensor 837 in the airflow direction 845. The sensor 837 can be coupled to the support structure 835. In one embodiment, the sensor 837 can be electrically coupled to the support structure 835. The first structure component 841 and the second structure component 839 can be coupled to the support structure 835. The first structure component 841 and the second structure component 839 can assist in securing the sensor 837 to the support structure 835. In another embodiment, the first structure component 841 and the second structure component 839 can each comprise an upper surface adjacent to an upper surface of the sensor 837. The first support structure 841 and the second support structure 839 can be used to assist in directing an airflow over the sensor 837 and to minimize air currents that could be disruptive or otherwise unwanted when air is passed over the sensor 837. The upper housing can comprise a variety of materials. In one embodiment, the upper housing can comprise plastic. In another embodiment, the upper housing can comprise tape placed over the flow channel. In yet other embodiments, the upper housing can comprise any other material that can withstand deformation from air flowing through the airflow pathway.

Figure 12C:
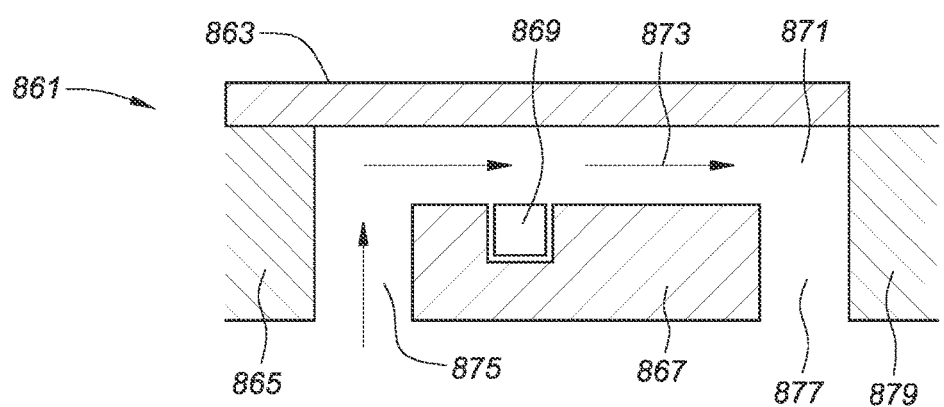

FIG. 12C depicts a schematic view of another embodiment of a flow channel 861. The flow channel 861 can comprise an upper housing 863, a first side support structure 865, a second side support structure 879, a sensor support structure 867, a sensor 869, an airflow pathway 871, an airflow sensor entrance 875, and an airflow sensor exit 877. The upper housing 863, the first side support structure 865, the second side support structure 879, the sensor support structure 867, and the sensor 869 can define the airflow pathway 871. The first side support structure 865 and the sensor support structure 867 can define an airflow sensor entrance 875. The sensor support structure 867 and the second side support structure 879 can define an airflow sensor exit 877. Air entering the flow channel 861 can enter through the airflow sensor entrance 875, can pass over the sensor 869, and can exit through the airflow sensor exit 877 in the airflow direction 873. As described above, the sensor 869 can be placed within a depression in the sensor support structure 867. The upper housing can comprise a variety of materials. In one embodiment, the upper housing can comprise plastic. In another embodiment, the upper housing can comprise tape placed over the flow channel. In yet other embodiments, the upper housing can comprise any other material that can withstand deformation from air flowing through the airflow pathway.

Figure 13:
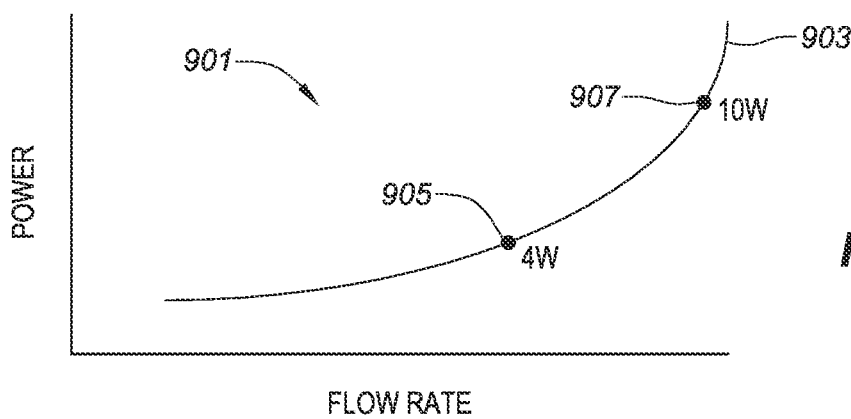
FIG. 13 is a graph illustrating one embodiment of the power delivered for various flow rates.
Figure 14:
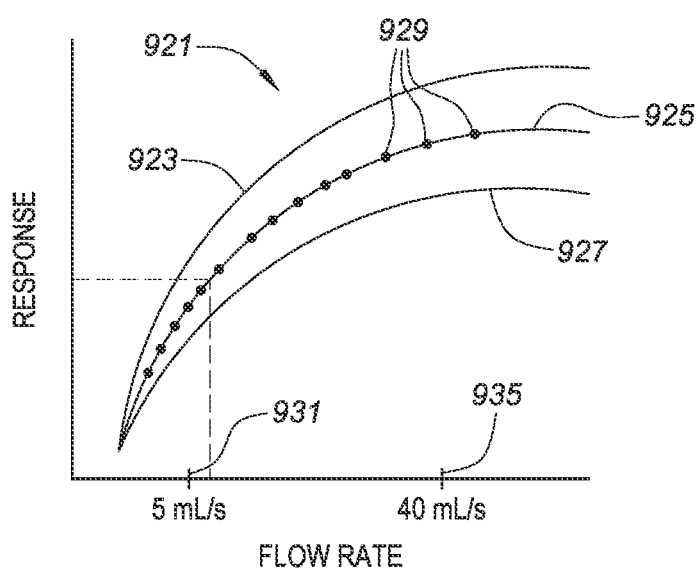
FIG. 14 is a graph illustrating several embodiments of response signals for various flow rates.
Figure 15:
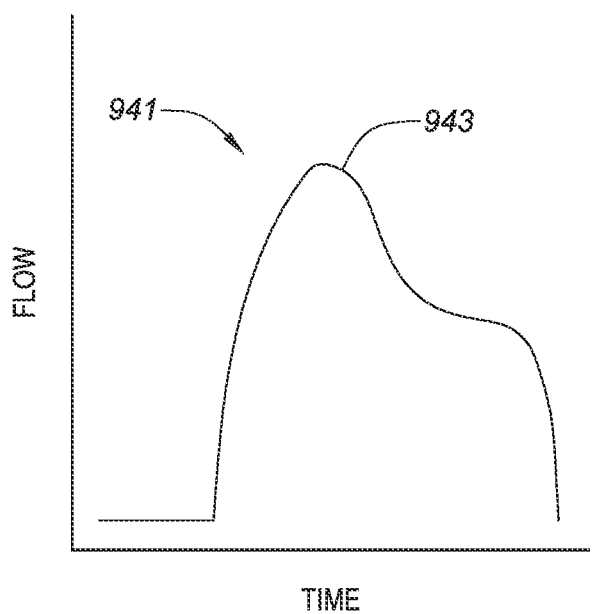
FIG. 15 is a graph illustrating one embodiment of a flow rate over time.
Figure 16:
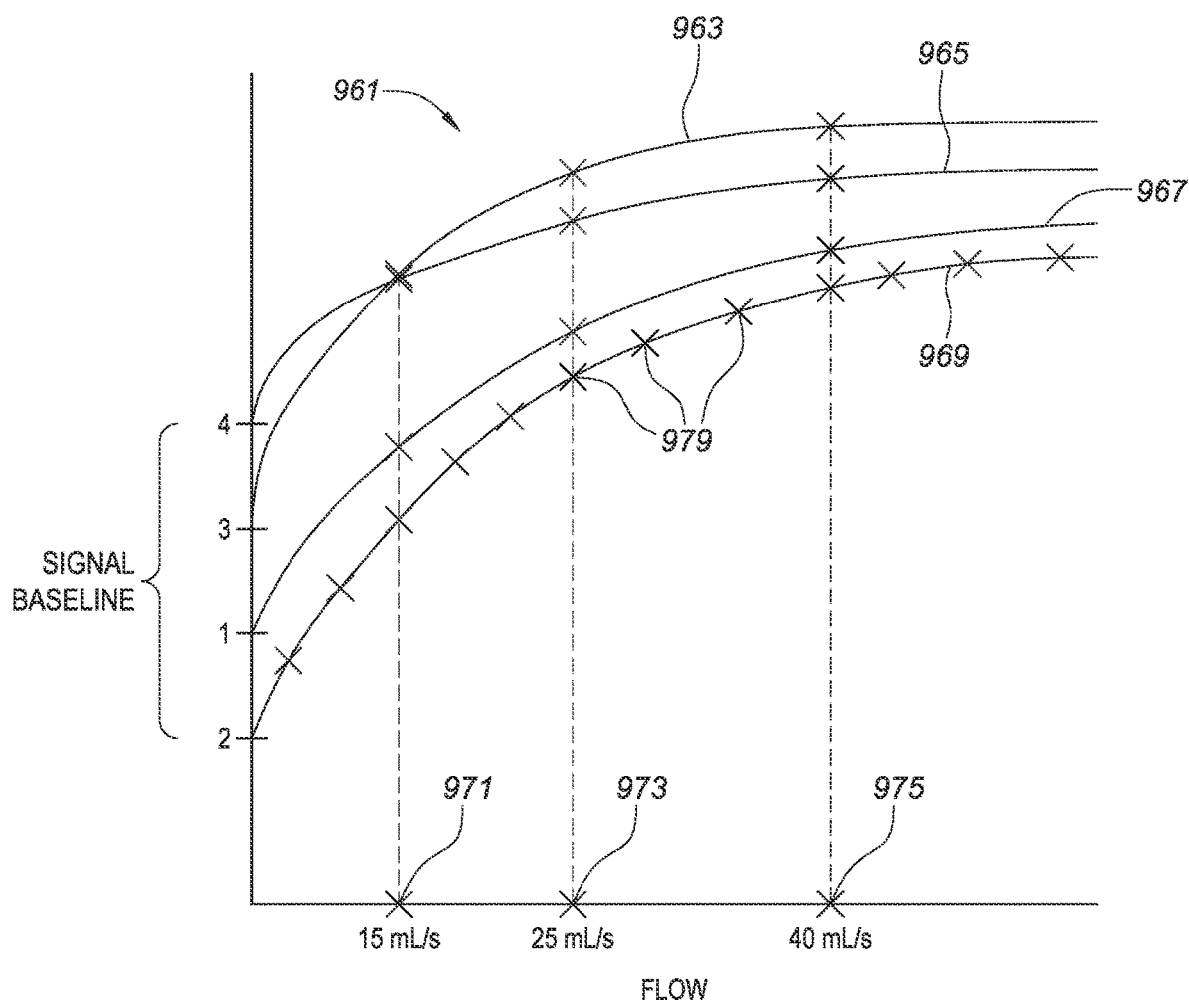
FIG. 16 is a graph illustrating several embodiments of response signals for various flow rates.

FIG. 13 depicts a graph illustrating one embodiment of the power delivered for a given flow rate 901. The depicted graph illustrates a response curve 903 showing a logarithmic graph with a power level for a sensed airflow rate. As seen in in the illustrated embodiment, a first position 905 on the graph comprises a power level of 4 W that can be output to an atomizer at a first flow rate. A second position 907 on the graph comprises a power level of 10 W that can be output to an atomizer at a second flow rate. The response curve comprises a logarithmic curve where the power output is exponential in response to the flow rate. An exponential increase in power output can be used as an atomizer may not be properly heated with an increasing rate of airflow using a linear response. In other embodiments, the power output can be increased in an exponential fashion in response to an increased airflow so that the atomizer can deliver a larger amount of aerosol in response to a larger or faster rate of airflow over the sensor and through the system as a whole. The larger amount of aerosol produced by the atomizer can attempt to mimic the increased amount of smoke that can be produced by a user who takes a deeper or longer drag on a traditional cigarette. In another embodiment, where an increase in aerosol is not desired, the power output can comprise a linear increase as airflow is increased.

FIG. 14 depicts a graph illustrating several embodiments of response to flow rate 921. The response illustrated in FIG. 14 is the response from the airflow sensor for a given flow rate. The graph illustrates a first response curve 923, a second response curve 925, and a third response curve 927. Each of the first response curve 923, the second response curve 925, and the third response curve 927 illustrate a response from different individual airflow sensors. The second response curve 925 further depicts a plurality of response points 929. The plurality of response points can each individually comprise a known response for a given flow rate. In another embodiment, only a portion of the plurality of response points 929 can be determined during testing and other of the plurality of response points 929 can be determined by calculating a curve to fit the determined response points. As shown in FIG. 14, a first response flow rate 931 can comprise a 5 ml/s flow rate and a second response flow rate 935 can comprise a 40 ml/s flow rate.

FIG. 15 depicts a graph illustrating one embodiment of a flow v time output 941. The flow v time output 941 comprises a user puff 943. The user puff 943 comprises a varying flow rate over time. As shown in the depicted user puff 943, initially the flow rate is negligible. At a later time, a user initiates the puff, and the flow rate increases until it reaches a maximum flow rate. The flow rate then slowly lowers over the course of time, until dropping back to the initial negligible flow rate.

FIG. 16 depicts a graph illustrating several embodiments of response to flow rate 961. As seen in FIG. 14, the response illustrated is the response from the airflow sensor for a given flow rate. The graph illustrates a first response curve 963, a second response curve 965, a third response curve 967, and a fourth response curve 969. Each of the first response curve 963, the second response curve 965, the third response curve 967, and the fourth response curve 969 illustrate a response from different individual airflow sensors. As seen in the illustrated embodiments, all of the sensors have different curves and different baseline conditions. The signals from each sensor can then be driven higher or lower to bring each sensor to a common baseline signal. Even after a common baseline signal has been assigned, each sensor still displays a different curve. The curve for each sensor can be calculated by determining the response signal for a subset of airflow rates. In one embodiment, three response signals can be determined to calculate the response curve. In the illustrated embodiment, the response signals can be determined at a first response location 971, a second response location 973, and a third response location 975. In one embodiment the three response signals can be recorded at 15 ml/s, 25 ml/s, and 40 ml/s. The response signal received at each of the three flow rates can be used to calibrate the response curve.

Each of the sensors comprises a response curve that is logarithmic or exponential. The response curve can be used to generate a table of points 979 that can be looked up by the system. The number of points within the look up table can vary. In one embodiment, the look up table can comprise 32 values. Other embodiments can have fewer or more points within the look up table. In another embodiment, an equation can be used to determine a flow rate for a specific signal. In another embodiment, the look up table can be limited in maximum range to what can be performed by a user using the device. In one embodiment, that upper range can comprise 40 ml/s to 50 ml/s. Further, the lowest airflow that an average user will be able to sustain for a light puff is about 15 ml/s. As a result, the normal range that can be used within the lookup table is 15 ml/s to 40 ml/s. In another embodiment, the normal range that can be used within the lookup table is 15 ml/s to 50 ml/s. In yet another embodiment, the normal range that can be used is 5 ml/s to 50 ml/s. In yet other embodiments, other ranges can be used. In one embodiment, the responsiveness can be scaled in terms of power output within that range. In another embodiment, an airflow rate above 35 ml/s will not increase a power output to the atomizer. In yet another embodiment, an airflow rate below 15 ml/s will not decrease the power output to the atomizer. Further, in one embodiment, the values included in the look up table are not evenly spread out. In this embodiment, the values above 35 ml/s can be further apart than those below 35 ml/s. In another embodiment, a threshold airflow rate of 5 ml/s can be used to start a puff event. While 5 ml/s airflow rate can be used to start a puff event, the coil does not energize until an airflow rate of 10 ml/s occurs. In one embodiment, the baseline value ceases updating after the puff event starts at 5 ml/s. Further, in another embodiment, the atomizer starts energizing at 10 ml/s, and then once the airflow rate decreases below 10 ml/s, the atomizer stops energizing. Further, the puff event stops after the airflow rate drops below 5 ml/s. Further, in other embodiments, the energization and puff event values can comprise different amounts than those listed herein.

Figure 17:
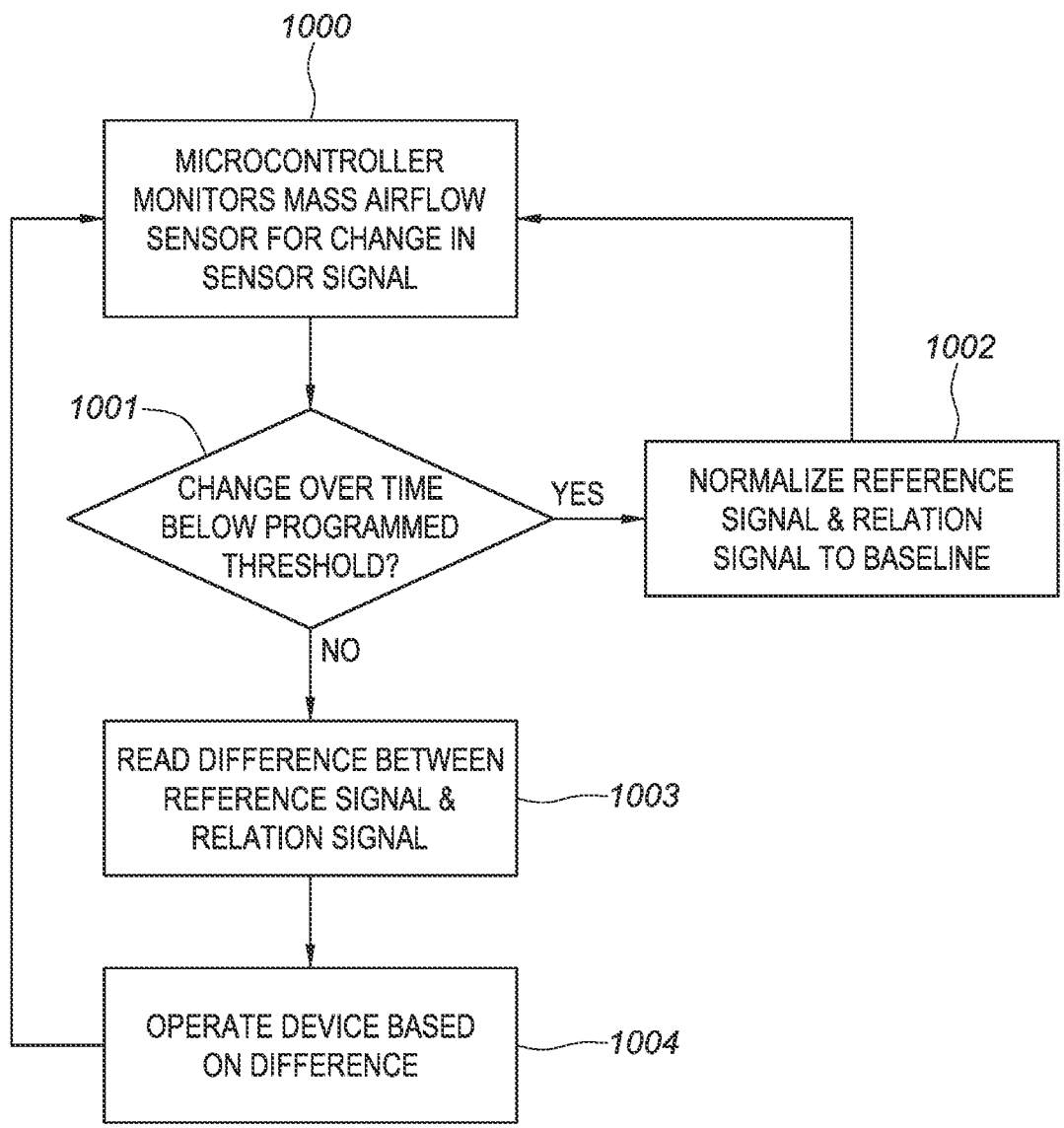
FIG. 17 is a flowchart illustrating one embodiment of a process for interpreting signals according to the disclosure.

FIG. 17 illustrates a flow-chart of the process by which the microcontroller or other component can interpret signals from the mass airflow sensor or other device. In step 1000 a microcontroller can monitor a sensor signal sent from the mass airflow sensor. When the microcontroller monitors a change in the sensor signal that is being monitored in step 1000, the microcontroller can determine if the change in the sensor signal is below a programmed threshold 1001. If the change in the sensor signal over a length of time is below the programmed threshold the microcontroller or other component can alter a reference signal and a relation signal to a predetermined baseline 1002. In one embodiment the reference signal can be set to a baseline reading of 2.0 volts. The microcontroller than continues to monitor the mass airflow sensor for a change in the sensor signal 1000. If the change in the sensor signal over time is above a programmed threshold 1001, then the microcontroller or other component reads the difference between the reference signal and the relation signal 1003. In step 1004, the microcontroller or other component can operate a device, sensor, or other component according to the difference between the reference signal and the relation signal. The process then goes back to step 1000 and the microcontroller or other component continues to monitor the mass airflow sensor for a change in the sensor signal over time.

The sensor can drift as the temperature of the sensor increases. The drift can comprise about 0.1% per degree Celsius. While the drift can appear minimal, at higher end flow rates, because of the low overall signal, the small difference can make a big difference in the sensed airflow rate. To account for the temperature drift error two approaches can be used. The first approach is to add a thermistor to the sensor. This thermistor can be powered through the offset and the resistance of the thermistor can vary with temperature. The resistance can be sampled and the temperature of the sensor can be determined. The second approach can use the sensor itself and look at the value output by the sensor when a puff event starts and use this signal as a baseline. A baseline of when a puff event is not occurring and a signal output by the sensor when a puff event occurs. The baseline signal when a puff event is not occurring will tend to shift slightly. This shift can be correlated to temperature. In one embodiment, a look up table can be used to determine a temperature shift. In another embodiment, an algorithm can be used to determine a temperature shift. The temperature shift described herein can be used for any airflow sensor, including mass airflow sensors, capacitive sensors, or others as would be known to one of ordinary skill in the art.

Various embodiments of the present disclosure are directed to an electronic smoking device. The electronic smoking device can comprise a flow channel and an atomizer. The flow channel can comprise an incoming airflow opening, an incoming airflow pathway, a sensor assembly, and an outgoing airflow opening. The atomizer can be fluidly coupled to the flow channel. The flow channel can be configured to direct an airflow from the incoming airflow opening, through the incoming airflow pathway, over the sensor assembly, and through the outgoing airflow opening. The electronic smoking device can further be configured to pass the airflow, at least in part, over the atomizer. In a more specific embodiment, the electronic smoking device can further comprise an outgoing airflow pathway between the sensor assembly and the outgoing airflow opening. In a more specific embodiment, the electronic smoking device can further comprise an external airflow pathway coupled to the flow channel, wherein the external airflow pathway is configured to direct air from the outgoing airflow opening to the atomizer.

In a more specific embodiment, the flow channel further comprises a first side wall, a second side wall, a bottom wall, and a top wall, and wherein the first side wall, the second side wall, the bottom wall, and the top wall define the incoming airflow opening. In a more specific embodiment, the flow channel is sized and configured to create a laminar flow of air in the incoming airflow pathway before the airflow reaches the sensor assembly. In some embodiments, the sensor assembly comprises a support structure and a sensor, and wherein the sensor is coupled to the support structure. In other embodiments, the sensor assembly further comprises a first layer and a second layer coupled to the support structure. In yet other embodiments, the first layer and the second layer create an upper surface. In other embodiments, the upper surface comprises a height above the support structure similar to a height of the sensor. In yet other embodiments, the upper surface is configured to minimize turbulence of the airflow over the sensor. In some embodiments, the first layer comprises copper. In other embodiments, the second layer comprises solder mask. In yet other embodiments, the sensor assembly further comprises a silkscreen material deposited on top of the second layer.

In another embodiment, the support structure comprises a PCB. In yet another embodiment, the support structure comprises a support depression. In other embodiments, a lower portion of the sensor is sized and configured to fit within the support depression. In some embodiments, the sensor assembly further comprises a sensor, and wherein the sensor comprises a height of no more than 0.2 mm.

Other various embodiments consistent with the present disclosure are directed to an electronic smoking device. The electronic smoking device can comprise a flow channel. The flow channel can comprise an incoming airflow opening, an incoming airflow pathway, a sensor assembly, and an outgoing airflow opening. The flow channel can be configured to direct an airflow from the incoming airflow opening, through the incoming airflow pathway, over the sensor assembly, and through the outgoing airflow opening. In other various embodiments, the flow channel is sized and configured to create a laminar flow of air in the incoming airflow pathway before the airflow reaches the sensor assembly. In yet other embodiments, the sensor assembly comprises a support structure, a first layer, a second layer, and a sensor, and wherein the sensor, the first layer, and the second layer are coupled to the support structure.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

The terms "including," "comprising" and variations thereof, as used in this disclosure, mean "including, but not limited to," unless expressly specified otherwise.

The terms "a," "an," and "the," as used in this disclosure, means "one or more," unless expressly specified otherwise.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS 10 electronic smoking device
12 end cap
14 power supply portion
16 atomizer/liquid reservoir portion
18 light-emitting diode (LED)
20 air inlets
22 battery
24 control electronics
26 airflow sensor
28 atomizer
30 heating coil
32 wick
34 central passage
36 liquid reservoir
38 air inhalation port
212 power supply portion
213 power supply portion sub-assembly
216 circumferential light guide
218 battery
220 LED
221 flexible printed circuit board
222 controller circuitry
224 airflow sensor
225 contacts
226 locking pin
227 airflow gasket
228 MAF gasket
229 spacer
240 upper sub-assembly housing
241 lower sub-assembly housing
242 wire lead
245 tube
246 tip diffuser
248 pattern
258 female connector port
320 microcontroller
322 driver
324 memory
326 microcomputer
328 interface
330 flow sensor
331 substrate
332 upstream thermopile
333 downstream thermopile
334 heater element
335 reference element
360 airflow signal
361 filter
362 gain amplifier
363 signal output
364 filter
370 upstream airflow signal
371 downstream airflow signal
372 first filter
373 second filter
374 difference amplifier
375 gain amplifier
376 offset
377 signal output
380 offset
440 microcontroller
441 data acquisition circuit
442 analog-to-digital converter
449 amplifier
450 mass airflow sensor
451 mass airflow heater
452 first thermopile
453 second thermopile
454 direction of airflow
456 heater
540 microcontroller
541 data acquisition circuit
542 analog-to-digital converter
549 amplifier
550 mass airflow sensor
551 mass airflow heater
552 thermopile
554 heater
556 heater
557 feedback resistor
558 gain resistor
601 flow channel
603 first side wall
605 second side wall
607 incoming airflow pathway
609 outgoing airflow pathway
611 incoming airflow opening
613 outgoing airflow opening
615 sensor assembly
617 sensor
619 airflow path
621 external airflow pathway
623 top wall
625 bottom wall
651 sensor assembly
653 support structure
655 sensor
659 first layer
661 second layer
663 upper surface
665 incoming portion
667 airflow pathway
701 sensor assembly
703 support structure
705 sensor
707 first structure component
709 second structure component
751 sensor assembly
753 support structure
755 sensor top portion
757 sensor base portion
759 sensor transition region
801 flow channel
803 upper housing
805 support structure
807 support depression
809 sensor
811 airflow pathway
813 airflow direction
831 flow channel
833 upper housing
835 support structure
837 sensor
839 second structure component
841 first structure component
843 airflow pathway
845 airflow direction
861 flow channel 863 upper housing
865 first side support structure
867 sensor support structure
869 sensor
871 airflow pathway
873 airflow direction
875 airflow sensor entrance
877 airflow sensor exit
879 second side support structure
901 power delivered for a given flow rate
903 response curve
905 first position
907 second position
921 response to flow rate
923 first response curve
925 second response curve
927 third response curve
929 plurality of response points
931 first response flow rate
935 second response flow rate
941 flow v time output
943 user puff
1000 microcontroller monitoring sensor
1001 change over time below threshold
1002 normalize reference signal and relation signal
1003 read difference between reference signal and relation signal
1004 operate device

We claim:

1. A vaporizer comprising:
an atomizer and liquid reservoir portion comprising a heating coil wrapped around a wick, the heating coil and wick positioned perpendicular to a longitudinal axis of the vaporizer;
a power supply portion including a subassembly housing in a tube, the subassembly housing holding a battery;
a plurality of light emitting diodes towards a first end of the subassembly housing;
a circuit board and an air flow sensor at a second end of the subassembly housing;
a flex circuit extending over the battery, the flex circuit electrically connecting the light emitting diodes to the circuit board;
the subassembly housing configured to be inserted into an open end of the tube;
the atomizer and liquid reservoir portion attached at the second end of the tube; and
electrical contacts electrically connected to the circuit board and extending radially outward toward apertures in a cylindrical sidewall of the tube.

2. The vaporizer of claim 1 further including a gasket extending around at least a portion of the air flow sensor.

3. The vaporizer of claim 1 further including a light guide at the first end of the tube.

4. The vaporizer of claim 1 wherein the subassembly housing conforms to a cylindrical shape of the battery.

5. A vaporizer comprising:
an atomizer and liquid reservoir portion comprising a heating coil wound on a wick, the wick having at least one end abutting or extending into a liquid reservoir, the heating coil and wick perpendicular to a longitudinal axis of the vaporizer;
a power supply portion including a tube having a first end and a second end, and a subassembly housing having a first end and a second end, the subassembly housing supporting a battery and a printed circuit board;
a plurality of light emitting diodes at a first end of the subassembly housing, the light emitting diodes electrically connected to the printed circuit board by a flex circuit extending alongside of the battery;
the subassembly housing configured to be longitudinally inserted into the tube to position the printed circuit board, and an air flow sensor electrically connected to the printed circuit board, towards a second end of the tube;
a light guide at the first end of the tube, the light guide configured to convey light from at least one of the light emitting diodes, wherein the at least one light emitting diode provides a visual indication by varying brightness, color, and/or on/off time, the visual indication associated with a functional aspect of the vaporizer;
the atomizer and liquid reservoir portion attached to the second end of the tube; and
electrical contacts electrically connected to the printed circuit board and extending radially outward, in a direction perpendicular to a longitudinal axis of the vaporizer, toward apertures in a cylindrical sidewall of the tube, the electrical contacts providing an electrical connection between an external charging circuit and the battery.

6. The vaporizer of claim 5 wherein a gasket contacts the subassembly housing and the printed circuit board and forms part of an airflow passage within the vaporizer.

7. The vaporizer of claim 6 wherein the printed circuit board gasket seals against the printed circuit board and directs airflow past the air flow sensor.

8. A vaporizer comprising:
an atomizer and liquid reservoir portion;
a power supply portion attachable to the atomizer and liquid reservoir portion, the power supply portion including a subassembly housing in a tube, the subassembly housing holding a battery and configured to be inserted into an open end of the tube;
a circuit board and an air flow sensor on the subassembly housing;
a flex circuit extending over the battery, the flex circuit electrically connecting the circuit board; and
electrical contacts electrically connected to the circuit board and extending radially outward, in a direction perpendicular to a longitudinal axis of the vaporizer, toward apertures in a cylindrical sidewall of the tube, the electrical contacts providing an external electrical connection for charging the battery.

* * * * *